United States Patent [19]

Tanaka et al.

[11] 4,309,432
[45] Jan. 5, 1982

[54] COMPOSITIONS FOR TREATING GLAUCOMA CONTAINING A CARBOSTYRIL

[75] Inventors: Nobuyuki Tanaka, Tokushima; Yoichi Nishinakamura, Ibaragi; Kazuyuki Nakagawa, Tokushima, all of Japan

[73] Assignee: Otsuka Pharmaceutical Company, Ltd., Tokyo, Japan

[21] Appl. No.: 109,057

[22] Filed: Jan. 2, 1980

[30] Foreign Application Priority Data

Jan. 30, 1979 [JP] Japan ................. 54/10108
Jun. 6, 1979 [JP] Japan ................. 54/70361

[51] Int. Cl.$^3$ .............................. A61K 31/47
[52] U.S. Cl. ................................... 424/258
[58] Field of Search ........................... 424/258

[56] References Cited

U.S. PATENT DOCUMENTS

| | | |
|---|---|---|
| 3,910,924 | 10/1975 | Tamura et al. .............. 424/258 |
| 3,919,239 | 11/1975 | Nakagawa et al. .......... 424/258 |
| 3,953,456 | 4/1976 | Nakagawa et al. .......... 424/258 |
| 3,969,507 | 7/1976 | Kohri ........................... 424/258 |
| 3,975,391 | 8/1976 | Nakagawa et al. .......... 424/258 |
| 3,994,901 | 11/1976 | Nakagawa et al. .......... 424/258 |
| 4,081,447 | 3/1978 | Prasad et al. ................ 424/258 |
| 4,147,869 | 4/1979 | Nakagawa et al. .......... 424/258 |
| 4,210,753 | 7/1980 | Tominaga et al. ........... 424/258 |

FOREIGN PATENT DOCUMENTS

WO80/00215 2/1980 PCT Int'l Appl. .................. 424/258
55/2631 10/1980 Japan ................................ 424/258

OTHER PUBLICATIONS

Brit. J. Ophthal. (1977), pp. 301-303—Bonomi et al.
Chem. Abst. 77, 775(w) (1972)-Pecori—Giraldi et al.
Chem. Abst. 81, 131,068(y) (1974)—Stankiewicz et al.
Chem. Abst. 82, 38754(e) (1975)—Sharaf et al.

*Primary Examiner*—Douglas W. Robinson
*Attorney, Agent, or Firm*—Armstrong, Nikaido, Marmelstein & Kubovcik

[57] ABSTRACT

This invention provides a glaucoma treating composition comprising at least one of carbostyril derivatives represented by the formula

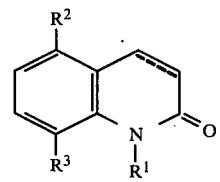

wherein $R^1$ is hydrogen, lower alkyl or lower alkenyl, $R^2$ is hydrogen or a group

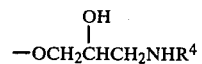

wherein $R^4$ is lower alkyl, cycloalkyl, or lower alkyl substituted by phenyl with or without a lower alkoxy substituent on the phenyl nucleus, $R^3$ is a group

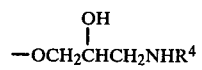

wherein $R^4$ is as defined above when $R^2$ is hydrogen, or $R^3$ is hydrogen, hydroxyl, ureido, lower alkynyloxy, lower alkoxy having a lower alkanoyl substitutent, lower alkanoylamino or lower alkenyloxy when $R^2$ is

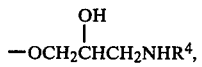

and the carbon-to-carbon bond between the 3-position and the 4-position of the carbostyril skeleton is a single bond or double bond, and pharmacologically acceptable acid addition salts thereof; and a method of treating glaucoma comprising administering said composition to a patient with glaucoma.

10 Claims, No Drawings

COMPOSITIONS FOR TREATING GLAUCOMA CONTAINING A CARBOSTYRIL

This invention relates to compositions for treating glaucoma.

Glaucoma is attributable basically to a sustained or repeated increase in the intraocular pressure and causes functional and further organic disorders to the eye. For the treatment of this disease, it is considered to be a matter of urgency to reduce the increased intraocular pressure to the normal level to maintain the proper visual function (Masakichi Mikuni and Kazuo Iwata, "Glaucoma," Kanehara Shuppan Co., Ltd., 1968).

Heretofore known as active compounds for use in glaucoma treating compositions are alkaloids such as pilocarpine, carbacholine, etc. and cholinesterase inhibitors such as eserine, neostigmine, demecarium, organic phosphorous compounds including, for example, isoflurophate (diisopropyl fluorophosphate) and echothiopate iodide, etc.

An object of this invention is to provide novel glaucoma treating compositions comprising compounds falling into a category entirely different from the above-mentioned known active compounds.

Another object of the invention is to provide useful glaucoma treating compositions which have incorporated therein such a specific compound and which are of low toxicity but effective for reducing intraocular pressure.

Another object of the invention is to provide glaucoma treating compositions which have incorporated therein such a specific compound as the active component and which are especially well suited for use as ophthalmic solutions.

Still another object of the invention is to provide a method of treating glaucoma with the abovementioned specific compound.

These and other objects of this invention will become apparent from the following description.

The present invention provides a glaucoma treating composition characterized in that the composition contains a pharmacologically effective amount of a carbostyril derivative represented by the formula (I)

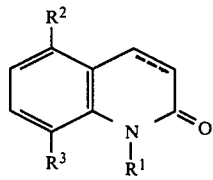
(I)

wherein
R$^1$ is hydrogen, lower alkyl or lower alkenyl,
R$^2$ is hydrogen or a group

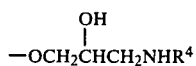

wherein R$^4$ is lower alkyl, cycloalkyl, or lower alkyl substituted by phenyl with or without a lower alkoxy substituent on the phenyl nucleus,
R$^3$ is a group

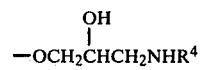

wherein R$^4$ is as defined above when R$^2$ is hydrogen, or R$^3$ is hydrogen, hydroxyl, ureido, lower alkynyloxy, lower alkoxy having a lower alkanoyl substitutent, lower alkanoylamino or lower alkenyloxy when R$^2$ is

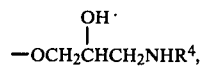

and the carbon-to-carbon bond between the 3-position and the 4-position of the carbostyril skeleton is a single bond or double bond, or
a pharmacologically effective amount of a pharmacologically acceptable acid addition salt of the derivative.

This invention has been accomplished based on the finding that the compounds represented by the above formula (I) and belonging to a category entirely different from the effective components of known glaucoma treating compositions act effectively for depressing intraocular pressure as glaucoma treating agents and are of low toxicity and usable with safety without giving any side effect.

Compounds of the formula (I) are disclosed, for example, in Laid-Open German Patent Publications (DT-OS) Nos. 2302027 and 2711719 and U.S. Pat. Nos. 3,953,456, 4,081,447 and 4,147,869, or can be easily prepared by the processes disclosed in these publications, for example, by reacting epichlorohydrin with a suitable hydroxycarbostyril derivative and reacting a suitable amine with the resulting 2,3-epoxy-propoxy compound or 3-chloro-2-hydroxy-propoxy compound, or mixture of such compounds. The publications state that the series of compounds represented by the formula (I) are effective as agents for treating arrhythmia and angina pectoris and also as hypotensive drugs, but nothing whatever is disclosed therein about the intraocular pressure decreasing activity of the compounds and the possible use of the compounds as glaucoma treating agents.

The lower alkyl groups contained in the compounds of the formula (I) are straight-chain or branched-chain alkyl groups having 1 to 4 carbon atoms and include, for example, methyl, ethyl, propyl, isopropyl, butyl, tert-butyl, etc.

The lower alkenyl groups are straight-chain or branched-chain alkenyl groups having 2 to 4 carbon atoms and include, for example, vinyl, allyl, crotyl, 1-methylallyl, etc.

The cycloalkyl groups are those having 3 to 8 carbon atoms and include cyclopropyl, cyclopentyl, cyclohexyl, cyclooctyl, etc.

The lower alkyl groups substituted by phenyl with or without a lower alkoxy substituent on the phenyl nucleus are those comprising a straight-chain or branched-chain alkylene group with 1 to 4 carbon atoms and a phenyl group attached to the alkylene group and having or not having on the phenyl nucleus 1 to 3 straight-chain or branched-chain alkoxy groups with 1 to 4 carbon atoms. Examples of such lower alkyl groups are benzyl, α-phenethyl, β-phenethyl, 4-phenylbutyl, 1,1- dimethyl-2-phenylethyl, β-3,4-dimethoxyphenethyl, 4-methoxybenzyl, β-3,4,5-trimethoxyphenethyl, etc.

The lower alkynyloxy groups are those having 2 to 4 carbon atoms and including ethynyloxy, propynyloxy, butynyloxy, 2-methylpropynyloxy, etc.

The lower alkoxy groups having a lower alkanoyl substituent are those having 1 to 4 carbon atoms and an alkanoyl substituent with 2 to 5 carbon atoms. Examples of such lower alkoxy groups are methylcarbonylmethoxy, 2-methylcarbonylethoxy, 2-ethylcarbonylethoxy, 3-methylcarbonylpropoxy, 4-methylcarbonylbutoxy, ethylcarbonylmethoxy, butylcarbonylmethoxy, 4-butylcarbonylbutoxy, etc.

The lower alkanoylamino groups are straight-chain or branched-chain alkanoylamino groups with 1 to 4 carbon atoms, such for example as formylamino, acetylamino, propionylamino, butyrylamino, etc.

The lower alkenyloxy groups are straight-chain or branched-chain alkenyloxy groups with 2 to 4 carbon atoms, such as vinyloxy, allyloxy, crotyloxy, 1-methylallyloxy, etc.

The acid addition salts of the carbostyril derivatives of the formula (I) are those usually acceptable pharmacologically. Examples of useful salts are salts of inorganic or organic acids, such as hydrochloric acid, sulfuric acid, nitric acid, hydrobromic acid, oxalic acid, maleic acid, fumaric acid, citric acid, tartaric acid, etc.

Among the compounds of the formula (I) and the pharmacologically acceptable acid addition salts thereof useful as the active components of the glaucoma treating compositions of this invention, especially preferable are those represented by the formula (I) in which $R^1$ and $R^3$ are each hydrogen, $R^2$ is a group

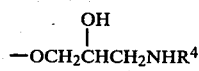

wherein $R^4$ is lower alkyl, and the carbon-to-carbon bond between the 3-position and the 4-position of the carbostyril skeleton is a single bond. These preferred compounds are represented by the formula (I-a)

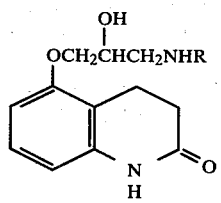

in which R is lower alkyl.

Other preferred compounds are those represented by the formula (I-a) in which the carbon-to-carbon bond between the 3-position and the 4-position of the carbostyril skeleton is a double bond.

Given below are typical examples of compounds represented by the formula (I) and useful as the active components of the glaucoma treating compositions of this invention.

5-(2-Hydroxy-3-tert-butylamino)propoxy-3,4-dihydrocarbostyril 5-(2-Hydroxy-3-isopropylamino)propoxy-3,4-dihydrocarbostyril 5-(2-Hydroxy-3-ethylamino)propoxy-3,4-dihydrocarbostyril 5-[2-Hydroxy-3-(β-3,4-dimethoxyphenetylamino)]-propoxy-3,4-dihydrocarbostyril 8-Methylcarbonylmethoxy-5-[2-hydroxy-3-(β-3,4-dimethoxyphenetylamino)]propoxy-3,4-dihydrocarbostyril 8-Hydroxy-5-[2-hydroxy-3-(β-3,4-dimethoxyphenetylamino)]propoxy-3,4-dihydrocarbostyril 5-(2-Hydroxy-3-benzylamino)propoxy-3,4-dihydrocarbostyril 5-(2-Hydroxy-3-cyclohexylamino)propoxy-3,4-dihydrocarbostyril 1-Ethyl-5-(2-hydroxy-3-cyclohexylamino)propoxy-3,4-dihydrocarbostyril 8-(2-Hydroxy-3-isopropylamino)propoxy-3,4-dihydrocarbostyril 8-(2-Hydroxy-3-cyclohexylamino)propoxy-3,4-dihydrocarbostyril 8-[2-Hydroxy-3-(β-3,4-dimethoxyphenethylamino)]-propoxy-3,4-dihydrocarbostyril 8-(2-Hydroxy-3-tert-butylamino)propoxy-3,4-dihydrocarbostyril 8-Ureido-5-[2-hydroxy-3-(β-3,4-dimethoxyphenethylamino)]propoxy-3,4-dihydrocarbostyril 8-Ureido-5-(2-hydroxy-3-tert-butylamino)propoxy-3,4-dihydrocarbostyril 8-Propynyloxy-5-[2-hydroxy-3-(β-3,4-dimethoxyphenethylamino)]propoxy-3,4-dihydrocarbostyril 8-Propynyloxy-5-(2-hydroxy-3-cyclohexylamino)-propoxy-3,4-dihydrocarbostyril 8-Ureido-5-(2-hydroxy-3-cyclohexylamino)propoxy-3,4-dihydrocarbostyril 8-Propynyloxy-5-(2-hydroxy-3-tert-butylamino)-propoxy-3,4-dihydrocarbostyril 8-Butynyloxy-5-[2-hydroxy-3-(β-3,4-dimethoxyphenethylamino)]propoxy-3,4-dihydrocarbostyril 8-Hydroxy-5-(2-hydroxy-3-tert-butylamino)propoxy-3,4-dihydrocarbostyril 8-Hydroxy-5-(2-hydroxy-3-cyclohexylamino)propoxy-3,4-dihydrocarbostyril 8-Methylcarbonylmethoxy-5-(2-hydroxy-3-tert-butylamino)propoxy-3,4-dihydrocarbostyril 8-Methylcarbonylmethoxy-5-(2-hydroxy-3-cyclohexylamino)propoxy-3-4-dihydrocarbostyril 8-Ethylcarbonylmethoxy-5-(2-hydroxy-3-isopropylamino)propoxy-3,4-dihydrocarbostyril 8-(4-Butylcarbonylbutoxy)-5-[2-hydroxy-3-(β-3,4-dimethoxyphenethylamino)]propoxy-3,4-dihydrocarbostyril 5-(2-Hydroxy-3-cyclooctylamino)propoxy-3,4-dihydrocarbostyril 8-Methylcarbonylmethoxy-5-[2-hydroxy-3-(4-phenylbutylamino)]propoxy-3,4-dihydrocarbostyril 8-Propynyloxy-5-[2-hydroxy-3-(β-3,4,5-trimethoxyphenethylamino)]propoxy-3,4-dihydrocarbostyril 8-Ureido-5-[2-hydroxy-3-(4-methoxybenzylamino)]-3,4-dihydrocarbostyril 1-Methyl-5-(2-hydroxy-3-tert-butylamino)propoxy-3,4-dihydrocarbostyril 1-Butyl-5-[2-hydroxy-3-(β-3,4-dimethoxyphenethylamino)]propoxy-3,4-dihydrocarbostyril 1-Methyl-8-methylcarbonylmethoxy-5-[2-hydroxy-3-(β-3,4-dimethoxyphenethylamino)]propoxy-3,4-dihydrocarbostyril 1-Methyl-8-hydroxy-5-(2-hydroxy-3-tert-butylamino)-propoxy-3,4-dihydrocarbostyril 8-Acetylamino-5-[2-hydroxy-3-(β-3,4-dimethoxyphenethylamino)]propoxy-3,4-dihydrocarbostyril 8-Propionylamino-5-(2-hydroxy-3-tert-butylamino)-propoxy-3,4-dihydrocarbostyril 8-Allyloxy-5-[2-hydroxy-3-($\beta$-3,4-dimethoxyphenethylamino)]propoxy-3,4-dihydrocarbostyril 1-Allyl-5-(2-hydroxy-3-tert-butylamino)propoxy-3,4-dihydrocarbostyril 1-Crotyl-5-(2-hydroxy-3-cyclohexylamino)propoxy-3,4-dihydrocarbostyril 1-Allyl-5-[2-hydroxy-3-($\beta$-3,4-dimethoxyphenethylamino)]propoxy-3,4-dihydrocarbostyril 1-Allyl-8-methylcarbonylmethoxy-5-[2-hydroxy-3-($\beta$-3,4-dimethoxyphenethylamino)]propoxy-3,4-dihydrocarbostyril 8-Allyloxy-5-(2-hydroxy-3-tert-butylamino)propoxy-3,4-dihydrocarbostyril 8-Crotyloxy-5-(2-hydroxy-3-cyclohexylamino)-propoxy-3,4-dihydrocarbostyril 5-(2-Hydroxy-3-tert-butylamino)propoxycarbostyril 5-(2-Hydroxy-3-isopropylamino)propoxycarbostyril 5-(2-Hydroxy-3-ethylamino)propoxycarbostyril 8-Methylcarbonylmethoxy-5-[2-hydroxy-3-($\beta$-3,4-dimethoxyphenethylamino)]propoxycarbostyril 5-(2-Hydroxy-3-cyclohexylamino)propoxycarbostyril 5-[2-Hydroxy-3-($\beta$-3,4-dimethoxyphenethylamino)]-propoxycarbostyril 1-Methyl-5-(2-hydroxy-3-tert-butylamino)propoxycarbostyril 8-Hydroxy-5-[2-hydroxy-3-($\beta$-3,4-dimethoxyphenethylamino)]propoxycarbostyril 8-Ureido-5-[2-hydroxy-3-($\beta$-3,4-dimethoxyphenethylamino)]propoxycarbostyril 8-Propynyloxy-5-[2-hydroxy-3-($\beta$-3,4-dimethoxyphenethylamino)]propoxycarbostril 8-Hydroxy-5-(2-hydroxy-3-tert-butylamino)propoxycarbostyril 8-(2-Hydroxy-3-cyclohexylamino)propoxycarbostyril 8-[2-Hydroxy-3-($\beta$-3,4-dimethoxyphenethylamino)]-propoxycarbostyril 8-(2-Hydroxy-3-tert-butylamino)propoxycarbostril The most preferable of the above compounds are 5-(2-hydroxy-3-tert-butylamino)propoxy-3,4-dihydrocarbostyril and 5-(2-hydroxy-3-tert-butylamino)-propoxycarbostyril.

The glaucoma treating compositions of this invention can be formulated as preparations suitable for administration, usually by admixing a derivative of the formula (I) or an acid addition salt thereof with an appropriate excipient or diluent for ophthalmic preparations. The compositions can be in the form of various usual preparations. They are usually adapted for topical administration for example, as ophthalmic ointments, solutions, etc. The compositions may be prepared in the form of tablets, granules, injection solutions, etc. for general administration. The compositions are most preferably administered in the form of ophthalmic solutions.

Although the dosage of the present compositions is not particularly limited, the compositions are usually given at a daily dose of about 0.01 to about 5 mg, preferably about 0.01 to about 1.0 mg, more preferably about 0.01 to about 0.5 mg, for the adult, calculated as the active component of the compositions. Preferably the compositions are administered in two to three divided daily doses. The amount of the active component contained in the compositions, although variable depending on the form of preparation, is preferably about 0.1 to about 70% by weight. The amount is preferably about 0.1 to about 2% by weight when the compositions are used for topical administration, for example, as ophthalmic solutions.

The compositions of this invention can be prepared in the usual manner with use of the carbostyril derivative of the formula (I) or an acid addition salt thereof as the active component, by admixing the active component with a suitable excipient and if required formulating the mixture into the desired form. The compositions, when formulated in the form of ophthalmic ointments or solutions or injection solutions, are further sterilized. Suitable excipients and diluents are selected for use in accordance with the form of the compositions. Examples of excipients useful for the preparation of ophthalmic ointments are emulsifiable excipients, water-soluble excipients, and suspendable excipients. Typical of such excipients are white vaseline, purified hydrous lanolin, liquid paraffin, etc. Typical of diluents for preparing ophthalmic solutions is sterile distilled water.

Solubilizing agents, stabilizers, buffers, antioxidants, preservatives, etc. can further be incorporated into the compositions of this invention. Examples of solubilizing agents useful for the preparation of ophthalmic solutions are sodium carboxymethyl cellulose; polyoxyethylene ethers such as polyoxyethylene lauryl ether and polyoxyethylene oleyl ether; higher fatty acid esters of polyethylene glycol such as polyethylene glycol monolaurate and polyethylene glycol monooleate; fatty acid esters of polyoxyethylene such as polyoxyethylene sorbitan monolaurate and polyoxyethylene sorbitan monooleate; etc. Examples of useful stabilizers are hydroxypropylmethyl cellulose, polyvinyl alcohol, carboxymethyl cellulose, hydroxyethyl cellulose, glycerin, EDTA, etc. Examples of useful buffers are sodium dihydrogenphosphate, disodium hydrogenphosphate, potassium hydrogenphosphate, boric acid, sodium borate, citric acid, sodium citrate, tartaric acid, sodium tartrate, etc. Examples of useful antioxidants are sodium bisulfite, sodium thiosulfite, ascorbic acid, etc. Examples of useful preservatives are chlorobutanol, benzethonium chloride, benzalkonium chloride, cetylpyridinium chloride, thimerosal, phenethyl alcohol, methyl p-hydroxybenzoate, propyl p-hydroxybenzoate, etc.

The compositions of this invention, when in the form of ophthalmic solutions, should preferably be made isotonic with tears. For this purpose, common salt or the like can be added to the compositions as desired. It is desirable to adjust the pH of the ophthalmic solutions to about 5.5 to about 8.5, preferably about 6.5 to about 7.5.

The glaucoma treating compositions of this invention thus prepared are given to patients by various methods in accordance with the form of the preparations. Ophthalmic solutions are applied dropwise to the eye from a suitable container or sprayed onto the eye from an applicator. Ophthalmic ointments are also applied to the eye. Tablets and granules are orally given, while injection solutions are administered subcutaneously, intramuscularly or intravenously. The desired therapeutic effect can be achieved in any of these cases.

The invention will be described below in greater detail with reference to preparation examples and medicinal efficacy test, to which the invention is not limited.

PREPARATION EXAMPLE 1

| | |
|---|---|
| 5-(2-Hydroxy-3-tert-butylamino)propoxy-3,4- | 10 mg |

-continued

| | |
|---|---|
| dihydrocarbostyril hydrochloride | |
| Benzethonium chloride | 0.1 mg |
| Sodium chloride | 3 mg |
| Sodium dihydrogenphosphate | 5 mg |
| Disodium hydrogenphosphate . 12 H$_2$O | 11.8 mg |
| Distilled water | Suitable amount |
| Total | 1 ml |

The ingredients are dissolved in distilled water, and the solution is filtered with suitable filter paper and sterilized to formulate a glaucoma treating composition of this invention in the form of an ophthalmic solution.

PREPARATION EXAMPLE 2

| | |
|---|---|
| 5-(2-Hydroxy-3-tert-butylamino)propoxy-carbostyril hydrochloride | 10 mg |
| Benzethonium chloride | 0.1 mg |
| Sodium chloride | 3 mg |
| Sodium dihydrogenphosphate | 5 mg |
| Disodium hydrogenphosphate . 12 H$_2$O | 11.8 mg |
| Distilled water | Suitable amount |
| Total | 1 ml |

In the same manner as in Preparation Example 1, an ophthalmic solution for treating glaucoma is prepared from the above ingredients according to the invention.

PREPARATION EXAMPLE 3

| | |
|---|---|
| 8-Methylcarbonylmethoxy-5-[2-hydroxy-3-($\beta$-3,4-dimethoxyphenethylamino)]propoxy-3,4-dihydrocarbostyril oxalate | 20 mg |
| Benzethonium chloride | 0.1 mg |
| Sodium chloride | 3 mg |
| Sodium dihydrogenphosphate | 5 mg |
| Disodium hydrogenphosphate . 12 H$_2$O | 11.8 mg |
| Distilled water | Suitable amount |
| Total | 1 ml |

In the same manner as in Preparation Example 1, an ophthalmic solution for treating glaucoma is prepared from the above ingredients according to this invention.

PREPARATION EXAMPLE 4

| | |
|---|---|
| 5-(2-Hydroxy-3-tert-butylamino)propoxy-3,4-dihydrocarbostyril hydrochloride | 10 mg |
| 10% Solution of benzalkonium chloride | 1 µl |
| Sodium chloride | 6.9 mg |
| Sodium dihydrogenphosphate | 0.4 mg |
| Disodium hydrogenphosphate . 12 H$_2$O | 1.0 mg |
| Distilled water | Suitable amount |
| Total | 1 ml |

In the same manner as in Preparation Example 1, an ophthalmic solution for treating glaucoma is prepared from the above ingredients according to this invention.

PREPARATION EXAMPLE 5

| | |
|---|---|
| 5-(2-Hydroxy-3-tert-butylamino)propoxy-3,4-dihydrocarbostyril hydrochloride | 20 mg. |
| 10% Solution of benzalkonium chloride | 1 µl |
| Sodium chloride | 5.0 mg |
| Sodium dihydrogenphosphate | 0.4 mg |
| Disodium hydrogenphosphate . 12 H$_2$O | 1.0 mg |
| Distilled water | Suitable amount |
| Total | 1 ml |

In the same manner as in Preparation Example 1, an ophthalmic solution for treating glaucoma is prepared from the above ingredients according to this invention.

EFFICACY TEST 1

Two drops of the ophthalmic solution obtained in Preparation Example 1 are instilled to the eye of three patients with glaucoma. The intraocular pressure is measured between 10 a.m. and 11 a.m. before the instillation and one day and two days after the instillation by Goldmann applanation tonometer. The results are listed in Table 1 below.

TABLE 1

| | | Intraocular pressure (mm Hg) | | |
|---|---|---|---|---|
| Patient | | Before instillation | 1 day later | 2 days later |
| A | Left eye | 42 | 16 | 16 |
| | Right eye | 26 | 18 | 14 |
| B | Left eye | 28 | 20 | 16 |
| | Right eye | 28 | 19 | 15 |
| C | Left eye | 28 | 18 | 13 |
| | Right eye | 15 | 12 | 12 |

Patient A—Instillation to the left eye affected with secondary glaucoma.
Patient B—Instillation to both eyes with open angle glaucoma.
Patient C—Instillation to the left eye suspected of glaucoma and affected with conjunctivitis and primary cataract.

Table 1 reveals that the composition of this invention has high activity to reduce intraocular pressure and is effective for treating glaucoma. An observation of the eye of the patient after the test indicates no abnormality due to the testing.

EFFICACY TEST 2

Two drops of the ophthalmic solution obtained in Preparation Example 2 are instilled to the eye of three patients with glaucoma. In the same manner as in Efficacy Test 1, the intraocular pressure is measured before the instillation and 1, 4 and 24 hours after the instillation. Table 2 shows the results.

TABLE 2

| | | Intraocular pressure (mm Hg) | | | |
|---|---|---|---|---|---|
| Patient | | Before instillation | 1 hour later | 4 hours later | 24 hours later |
| D | Left eye | 27 | 16 | 18 | 21 |
| | Right eye | 28 | 18 | 18 | 21 |
| E | Left eye | 41 | 38 | 22 | 17 |
| | Right eye | 25 | 20 | 20 | 18 |
| F | Left eye | 25 | 22 | 20 | 22 |
| | Right eye | 22 | 21 | 19 | 17 |

Patient D—Instillation to both eyes affected with simple glaucoma.
Patient E—Instillation to the left eye affected with secondary glaucoma.

Patient F—Instillation to the left eye affected with simple glaucoma.

Table 2, like Table 1, also reveals that the glaucoma treating composition of this invention produces an outstanding therapeutic effect. The eyes of the patients, when observed after the test, are found to be free of any abnormality due to the instillation of the composition.

EFFICACY TEST 3

Method

Male rabbits of New Zealand Albino strain, weighing 1.8 to 2.5 kg, are used as experimental animals. Intraocular pressure is measured with an Alcon pneumatic tonometer without local anesthesia, while holding the animal in a cylindrical rabbit holder.

The test compound is dissolved in a physiological solution of NaCl to a concentration of 1% (W/V), and the resulting solution is adjusted to a pH of 6.5 to 7.0 with a 0.01 N aqueous NaOH solution. The solution is instilled to one of the eyes of the animal in an accurate amount of 100 μl with a microsyringe after measuring the intraocular pressure of the eye. The eyelid is held closed for 1 minute after the instillation to prevent the escape of the solution.

The efficacy of the test compound is determined by measuring the intraocular pressure 30 minutes and 1 hour after the instillation and comparing the measurements with the pressure measured before the instillation. A 100 μl quantity of physiological saline containing no test compound is similarly tested on a control group. Table 3 shows the results.

TEST COMPOUNDS

Compound A: 5-(2-Hydroxy-3-tert-butylamino)-propoxy-3,4-dihydrocarbostyril hydrochloride Compound B: 5-(2-Hydroxy-3-tert-butylamino)propoxycarbostyril hydrochloride Compound C: 8-Methylcarbonylmethoxy-5-[2-hydroxy-3-(β-3,4-dimethoxyphenethylamino)]-propoxy-3,4-dihydrocarbostyril oxalate Compound D: 8-Hydroxy-5-[2-hydroxy-3-(β-3,4-dimethoxyphenethylamino)]propoxy-3,4-dihydrocarbostyril hydrochloride Compound E: 5-(2-Hydroxy-3-ethylamino)propoxy-3,4-dihydrocarbostyril maleate Compound F: 5-(2-Hydroxy-3-benzylamino)propoxy-3,4-dihydrocarbostyril hydrochloride Compound G: 5-(2-Hydroxy-3-cyclohexylamino)-propoxy-3,4-dihydrocarbostyril hydrochloride Compound H: 1-Ethyl-5-(2-hydroxy-3-cyclohexylamino)propoxy-3,4-dihydrocarbostyril hydrochloride Compound I: 8-(2-Hydroxy-3-isopropylamino)-propoxy-3,4-dihydrocarbostyril hydrochloride Compound J: 8-Ureido-5-[2-hydroxy-3-(β-3,4-dimethoxyphenethylamino)]propoxy-3,4-dihydrocarbostyril hydrochloride Compound K: 8-Propynyloxy-5-[2-hydroxy-3-(β-3,4-dimethoxyphenethylamino)]propoxy-3,4-dihydrocarbostyril oxalate Compound L: 8-Acetylamino-5-[2-hydroxy-3-(β-3,4-dimethoxyphenethylamino)]propoxy-3,4-dihydrocarbostyril hydrochloride Compound M: 8-Allyloxy-5-(2-hydroxy-3-tert-butylamino)propoxy-3,4-dihydrocarbostyril hydrochloride Compound N: 1-Allyl-5-(2-hydroxy-3-tert-butylamino)-propoxy-3,4-dihydrocarbostyril hydrochloride

TABLE 3

| Test compound | Animal No. | Intraocular pressure (mm Hg) | | |
|---|---|---|---|---|
| | | Before instillation | 30 minutes after instillation | 1 hour after instillation |
| A | 1 | 23 | 20 | 20 |
| | 2 | 22 | 17 | 18 |
| | 3 | 18 | 16 | 15 |
| | 4 | 19 | 16 | 16 |
| | 5 | 20 | 17 | 18 |
| | Average | 20.4 | 17.2 | 17.4 |
| B | 1 | 18 | 16 | 16 |
| | 2 | 18 | 18 | 17 |
| | Average | 18.0 | 17.0 | 16.5 |
| C | 1 | 20 | 18 | 17 |
| | 2 | 21 | 16 | 18 |
| | Average | 20.5 | 17.0 | 17.0 |
| D | 1 | 18 | 17 | 13 |
| | 2 | 18 | 17 | 15 |
| | Average | 18.0 | 17.0 | 14.0 |
| E | 1 | 20 | 19 | 18 |
| | 2 | 18 | 17 | 16 |
| | Average | 19.0 | 18.0 | 17.0 |
| F | 1 | 20 | 19 | 19 |
| | 2 | 19 | 18 | 18 |
| | Average | 19.5 | 18.5 | 18.5 |
| G | 1 | 17 | 16 | 16 |
| | 2 | 19 | 17 | 17 |
| | Average | 18.0 | 16.5 | 16.5 |
| H | 1 | 18 | 16 | 16 |
| | 2 | 18 | 15 | 15 |
| | Average | 18.0 | 15.5 | 15.5 |
| I | 1 | 18 | 17 | 16 |
| | 2 | 19 | 16 | 17 |
| | Average | 18.5 | 16.5 | 16.5 |
| J | 1 | 20 | 17 | 16 |
| | 2 | 19 | 18 | 18 |
| | Average | 19.5 | 17.5 | 17.0 |
| K | 1 | 20 | 19 | 18 |
| | 2 | 19 | 18 | 18 |
| | Average | 19.5 | 18.5 | 18.0 |
| L | 1 | 20 | 18 | 17 |
| | 2 | 19 | 18 | 18 |
| | Average | 19.5 | 18.0 | 17.5 |
| M | 1 | 20 | 19 | 18 |
| | 2 | 21 | 19 | 18 |
| | Average | 20.5 | 19.0 | 18.0 |
| N | 1 | 19 | 18 | 17 |
| | 2 | 18 | 17 | 16 |
| | Average | 18.5 | 17.5 | 16.5 |
| Physiological saline (control) | 1 | 21 | 21 | 21 |
| | 2 | 17 | 17 | 18 |
| | Average | 19 | 19 | 19.5 |

Table 3 reveals that the active compounds tested (Compounds A to N) produce approximately similar intraocular pressure reducing effects on normal rabbits. These results, as well as the preceding test results, indicate that the present compounds are highly effective for curing glaucoma.

Acute Toxicity Test

Active compounds useful for the glaucoma treating compositions of this invention are intravenously administered to mice to test the compounds for acute toxicity. Table 4 shows the $LD_{50}$ values determined.

TABLE 4

| Test No. | Compound | $LD_{50}$ (mg/kg) |
|---|---|---|
| 1 | A | 54.4 |
| 2 | B | 44.6 |
| 3 | C | 1260* |
| 4 | I | 81.6 |

| Test No. | Compound | LD$_{50}$ (mg/kg) |
| --- | --- | --- |
| 5 | J | 143 |

*Determined by the oral administration of Compound C to male rats.

Other active compounds of this invention are also tested for acute toxicity in the same manner as above, i.e., by intravenously administering them to mice. The LD$_{50}$ values determined are all not lower than about 40 mg/kg.

We claim:

1. An ophthalmic solution comprising about 0.1 to about 2% by weight of a compound of the formula:

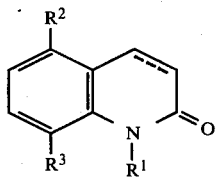

wherein R$^1$ is hydrogen, lower alkyl or lower alkenyl, R$^2$ is hydrogen or a group

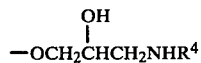

wherein R$^4$ is lower alkyl, cycloalkyl or lower alkyl substituted by phenyl or substituted by phenyl having a lower alkoxy substituent on the phenyl nucleus, R$^3$ is a group

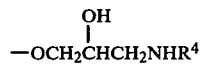

wherein R$^4$ is as defined above when R$^2$ is hydrogen, or R$^3$ is hydrogen, hydroxyl, ureido, lower alkynyloxy, lower alkoxy having a lower alkanoyl substituent, lower alkanoylamino or lower alkenyloxy when R$^2$ is

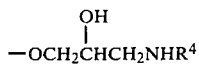

and the carbon-to-carbon bond between the 3-position and the 4-position of the carbostyril skeleton is a single bond or double bond or a pharmacologically acceptable acid addition salt thereof in combination with a diluent suitable for administration to the eye.

2. An ophthalmic solution of claim 1 wherein R$^1$ and R$^3$ are each hydrogen, R$^2$ is a group

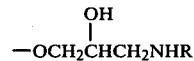

wherein R is lower alkyl, and the carbon-to-carbon bond between the 3-position and the 4-position of the carbostyril skeleton is a single bond, or pharmacologically acceptable acid addition salts thereof.

3. An ophthalmic solution of claim 2 wherein the active compound is 5-(2-hydroxy-3-tertbutylamino)-propoxy-3,4-dihydrocarbostyril.

4. An ophthalmic solution as of claim 1 wherein the diluent is water.

5. A method of treating glaucoma wherein the ophthalmic solution of claim 1 is topically administered to a patient with glaucoma.

6. A method of treating glaucoma wherein the ophthalmic solution of claim 3 is topically administered to the patient with glaucoma.

7. A method of treating glaucoma wherein the ophthalmic solution of claim 4 is topically administered to the patient with glaucoma.

8. The method of any one of claims 5 to 7 wherein the composition is instilled to the eye of the patient.

9. The method of claim 8 wherein the composition is instilled at a dose of about 0.01 to about 5 mg per day calculated as the compound for an adult.

10. The method of claim 9 wherein the composition is instilled at a dose of about 0.01 to about 0.5 mg per day calculated as the compound for an adult.

* * * * *

Disclaimer 4,309,432.—*Nobuyuki Tanaka*, Tokushima; *Yoichi Nishinakamura*, Ibaragi and *Kazuyuki Nakagawa*, Tokushima, Japan. COMPOSITIONS FOR TREATING GLAUCOMA CONTAINING A CARBOSTYRIL. Patent dated Jan. 5, 1982. Disclaimer filed Apr. 17, 1986, by the assignee, *Otsuka Pharmaceutical Co., Ltd.*

Hereby enters this disclaimer to claims 1, 2, 3 and 4 of said patent.
[*Official Gazette June 17, 1986.*]